United States Patent
Duan

(10) Patent No.: US 6,900,734 B2
(45) Date of Patent: May 31, 2005

(54) CAPILLARY-DISCHARGE BASED DETECTOR FOR CHEMICAL VAPOR MONITORING

(75) Inventor: Yixiang Duan, White Rock, NM (US)

(73) Assignee: The Regents of the Universtiy of California, Oakland, CA (US)

( * ) Notice: Subject to any disclaimer, the term of this patent is extended or adjusted under 35 U.S.C. 154(b) by 79 days.

(21) Appl. No.: 10/386,916

(22) Filed: Mar. 11, 2003

(65) Prior Publication Data

US 2004/0178917 A1 Sep. 16, 2004

(51) Int. Cl.[7] .............................................. G08B 17/10
(52) U.S. Cl. ...................... 340/632; 340/633; 423/210; 250/339.03
(58) Field of Search ................................ 340/630, 632, 340/633, 634, 577, 578, 579, 629; 250/339.03, 374, 389, 336, 423 P; 423/210, 235; 372/59, 60

(56) References Cited

U.S. PATENT DOCUMENTS

| | | | | |
|---|---|---|---|---|
| 3,951,607 A | * | 4/1976 | Fraser | .......................... 422/84 |
| 4,413,185 A | * | 11/1983 | Leveson et al. | ......... 250/423 P |
| 4,509,855 A | * | 4/1985 | Gay | ............................ 356/72 |
| 4,851,683 A | * | 7/1989 | Yang et al. | ............ 250/339.03 |
| 5,283,800 A | * | 2/1994 | Suzuki et al. | ................. 372/60 |
| 6,225,633 B1 | * | 5/2001 | Sun et al. | ................... 250/389 |
| 6,818,193 B2 | * | 11/2004 | Christodoulatos et al. | .. 423/210 |

* cited by examiner

*Primary Examiner*—Van T. Trieu
(74) *Attorney, Agent, or Firm*—John P. O'Banion

(57) ABSTRACT

A handheld/portable detector for chemical vapor monitoring includes a housing and a discharge chamber that is established therein. The plasma discharge has a relatively small volume, e.g., in the micro-liter range. A first electrode and a second electrode are disposed within the discharge chamber and a discharge gap is established therebetween. A sample gas tube is in fluid communication with the discharge chamber and provides a sample gas to the discharge chamber. Also, a plasma gas tube is in fluid communication with the discharge chamber and provides a plasma gas thereto. Accordingly, the plasma gas can be used to maintain microplasma discharge between the electrodes and the sample gas can be introduced into the microplasma discharge. A spectrometer optically connected to the handheld/portable detector is used to measure the radiation emitted by the sample gas when subjected to the microplasma discharge.

41 Claims, 9 Drawing Sheets

CAPILLARY-DISCHARGE BASED DETECTOR FOR CHEMICAL VAPOR MONITORING

STATEMENT REGARDING FEDERALLY SPONSORED RESEARCH OR DEVELOPMENT

This invention was made with Government support under Contract No. W-7405-ENG-36. The Government has certain rights in this invention.

CROSS-REFERENCE TO RELATED APPLICATIONS

Not Applicable

INCORPORATION-BY-REFERENCE OF MATERIAL SUBMITTED ON A COMPACT DISC

Not Applicable

BACKGROUND OF THE INVENTION

1. Field of the Invention

This invention pertains generally to devices for monitoring chemical vapor, and more particularly to handheld/portable devices for monitoring chemical vapor.

2. Description of Related Art

Chemical vapor emission is a growing problem in occupational safety and industrial hygiene. Workers are exposed to numerous volatile hazardous chemicals daily. This problem can be much more serious when an emission source is nearby, e.g., in a chemical production line. In such a case, frequent evaluation and daily monitoring of the hazardous chemical vapor emission is absolutely necessary as the control of chemical exposure has and continues to present a major environmental and occupational problem. In this case, sensitive, field-portable monitoring techniques are needed to identify and control these chemical vapor emissions. The ability to monitor before, during, and after production processes is also necessary to provide experimental data for decisions regarding occupational safety and industrial hygiene.

Conventional portable and in-situ instruments for monitoring chemical vapors have certain limitations including limited selectivity, poor sensitivity, and limited quantitative capabilities. Laboratory-based instruments such as gas chromatography coupled with mass spectrometry (GC/MS) can provide the needed analytical power, but GC/MS is not amenable to timely response in the field. In most cases, several hours are needed to complete chemical vapor analyses using laboratory equipment. Existing portable GC/MS is powerful, but it can be complex to operate, difficult to maintain, expensive to build, and limited in portability and applicability. Chemical sensors based upon general physical or chemical properties typically rely upon non-specific detection, i.e., they are responsive only to changes in total vapor concentrations, and, therefore, they are not applicable to multi-component detection and can not be used in complex environmental conditions. In addition, such sensors can only provide incomplete information regarding the exact nature of the detected species, which makes it difficult to identify the chemical components in air emissions.

Ion mobility spectrometer (IMS) has long been considered as a potential tool for chemical vapor monitoring and chemical warfare detection since its advent in late 1960s. However, presently, the number of IMS instruments deployed as field monitors or detectors for real samples is still very limited because the instrument suffers problems of low resolution, poor selectivity, and severe memory effect. Other currently available portable instruments for chemical vapor monitoring are either low sensitivity or limited selectivity and can not meet the needs in chemical vapor monitoring.

Molecular emission spectrometry has long been used to quantify organic vapors. Various plasma sources have been used for molecular fragmentation and excitation, including microwave induced plasma, capacitively coupled plasma, inductively coupled plasma, and glow discharge. The advantage of these conventional plasmas is that they provide sufficient energy for molecular fragmentation and excitation. However, these plasmas usually need high power to run, from a few tens watts to thousands watts, and are unsuitable for portable detectors.

Accordingly, the present invention recognizes a clear requirement for a genuinely portable detector that can be applied for on-site chemical vapor and air emission monitoring.

BRIEF SUMMARY OF THE INVENTION

The present invention provides a capillary-discharge based, battery-powered, handheld/portable chemical vapor detector that is sensitive, powerful, rugged, simple, and inexpensive. By way of example, and not limitation, a handheld/portable detector according to the present invention comprises an air sampling pump and a capillary column for sampling and regulation, a microplasma discharge for sample fragmentation and excitation, and a palm-sized spectrometer for molecular emission detection. Optical beams are collected from the plasma source through a collimating lens and transferred to the spectrometer using an optical fiber. The microplasma can be maintained with a small amount of gas, such as helium or argon, nitrogen or air.

Since the plasma gases have high excitation potentials and generate highly energized metastable species inside the plasma, the plasma source can provide sufficient energy to excite targeted chemical species through Penning ionization and energy transfer. Since such a microplasma discharge can be designed within a capillary tube at a micro-liter level or larger, it can be sustained with a power as low as milli-watts to several watts. This low power feature allows the system to be powered with a regular dry-cell battery, making the detector very flexible for on-site use.

In one aspect of the present invention a handheld/portable detector for chemical vapor monitoring includes a housing and a discharge chamber that is established therein. In this aspect, the discharge chamber has a volume of micro-liter level (e.g., from approximately 0.1 to approximately 500 micro-liter). Moreover, a first electrode and a second electrode are disposed within the discharge chamber. The second electrode is slightly spaced from the first electrode such that a discharge gap is established therebetween. In this aspect of the present invention, a sample gas tube and a plasma gas tube are in fluid communication with the discharge chamber. Moreover, each of the electrodes has an exposure area at the square millimeter ($mm^2$) level.

In this aspect of the present invention, the handheld/portable detector also includes a collimating lens that is adjacent to the discharge chamber. An optical fiber is installed adjacent to the collimating lens. Accordingly, the collimating lens focuses optical emissions from the discharge chamber into the optical fiber. The optical fiber transmits the optical beam to a spectrometer.

In another aspect of the present invention, a handheld/portable detector for chemical vapor monitoring includes a housing and a discharge chamber established therein. In this aspect, the discharge chamber has a volume of micro-liter level (e.g., from approximately 0.1 to approximately 500 micro-liter). Moreover, a microplasma discharge is generated within the discharge chamber and the discharge chamber receiving a chemical vapor that is introduced into the microplasma discharge.

According to a further aspect of the invention, a handheld/portable detector for chemical vapor monitoring comprises an air sampling pump for sample introduction, a capillary column for separation, a capillary discharge-based microplasma as an energy source for molecular fragmentation and excitation, a small battery powered supply system, and a palm-sized spectrometer for molecular emission detection.

According to a still further aspect of the invention, the sampling pump is in fluid communication with the discharge chamber without use of the capillary column and there is no sample gas separation before entering to the discharge chamber.

In yet another aspect of the present invention, a system for monitoring chemical vapor includes a handheld/portable detector. The detector has a discharge chamber that has a volume of micro-liter level (e.g., from approximately 0.1 micro-liter to approximately 500 micro-liter). A plasma gas source and a sampling pump are in fluid communication with the discharge chamber. Moreover, a spectrometer is optically connected to the discharge chamber.

In still another aspect of the present invention, a method for monitoring chemical vapor includes providing a discharge chamber that has a volume of micro-liter level (e.g., from approximately 0.1 to approximately 500 micro-liter). Microplasma discharge is generated within the discharge chamber and sample gases are introduced into the microplasma discharge. The radiation emitted by the sample within the microplasma discharge is then measured.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Referring more specifically to the drawings, for illustrative purposes the present invention is embodied in the apparatus generally shown in FIG. 1 through FIG. 4 and described with reference to FIG. 1 through FIG. 9. It will be appreciated that the apparatus may vary as to configuration and as to details of the parts, and that the method may vary as to the specific steps and sequence, without departing from the basic concepts as disclosed herein.

Figure 1:
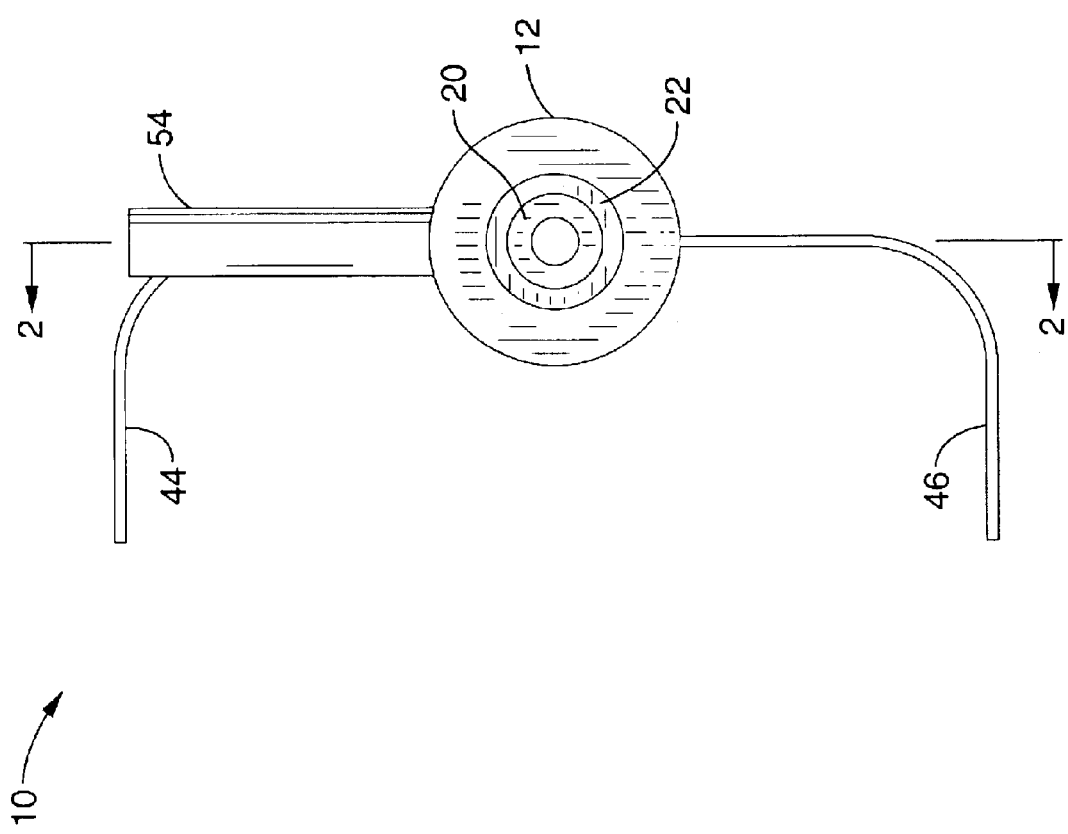
FIG. 1 is an end view of a handheld/portable detector for chemical vapor monitoring according to the present invention.
Figure 2:
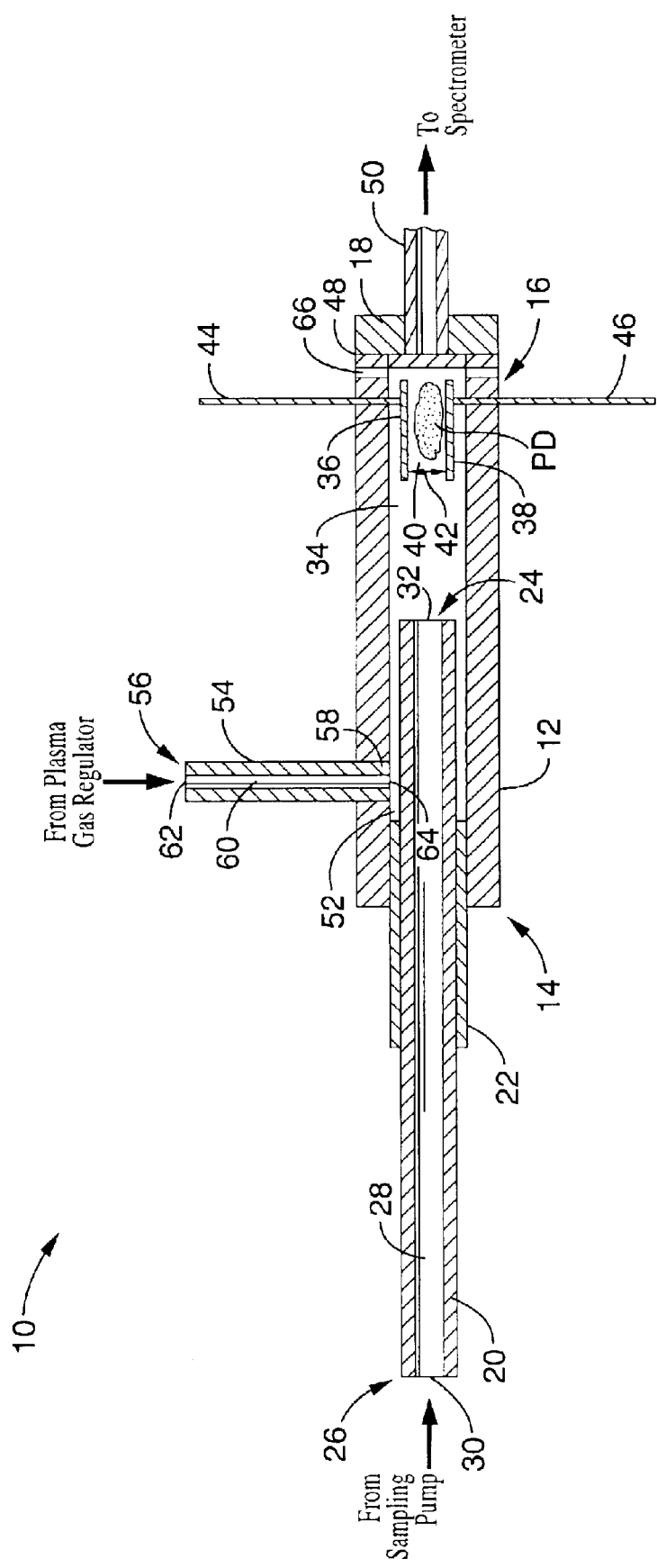
FIG. 2 is cross-section view of the handheld/portable detector for chemical vapor monitoring of FIG. 1 taken along line 2—2.

Referring initially to FIGS. 1 and 2, a capillary-discharge based handheld/portable detector for chemical vapor monitoring according to the present invention is shown and is generally designated 10. FIGS. 1 and 2 show that the handheld/portable detector 10 includes a hollow, generally cylindrical housing 12 having a proximal end 14 and a distal end 16. In a preferred embodiment, the housing 12 is fabricated from a non-conductive material such as Teflon® and comprises a capillary tube that has an inner diameter ranging from approximately one mm to approximately 10 mm.

As shown in FIG. 2 an end cap 18 covers the distal end 16 of the housing 12. A hollow, generally cylindrical sample gas inlet tube 20 extends from the proximal end 14 of the housing 12. The sample gas tube 20 is circumscribed by a hollow, generally cylindrical sealing collar 22 that is installed around the sample gas tube such that it effectively seals the interface between the gas sample tube and the housing 12.

FIG. 2 shows that the sample gas tube 20 has a proximal end 24 and a distal end 26. Moreover, the sample gas tube 20 has a sample gas passage 28 that has a sample gas inlet 30 and a sample gas outlet 32. As shown in FIG. 2, the handheld/portable detector 10 further comprises a discharge chamber 34 between the distal end 24 of the sample gas tube 20 and the end cap 18. It is to be understood that the sample gas tube 20 is in fluid communication with the discharge chamber 34 via the sample gas passage 28. Moreover, the sample gas tube 20 is in fluid communication with a sampling pump, described below. It is further to be understood that the plasma discharge (PD) has a volume in the micro-liter range (e.g., from less than approximately one micro-liter to several hundred micro-liters).

In a preferred embodiment, a first electrode 36 and a second electrode 38 are disposed within the discharge chamber 34. The electrodes 36, 38 are slightly spaced apart from each other so that a discharge gap 40 is established therebetween. As shown, the discharge gap 40 has a width 42. Moreover, a first conductor 44, such as a wire, is connected to the first electrode 36 and a second conductor 46, such as a wire, is connected to the second electrode 38. It is to be understood that the conductors 44, 46 are connected to a power source, described below, that is used to generate microplasma discharge between the electrodes 36, 38. It is also to be understood that each electrode 36, 38 has an exposure area from less than approximately one square millimeter to a level of several tens square millimeters. Accordingly, the microplasma generated between the electrodes 36, 38 is very small and can be easily maintained at atmospheric pressure with a small amount of plasma gas, such as helium, argon, nitrogen, or any other gases. The microplasma discharge can be used for the molecular fragmentation and excitation of chemical vapors introduced into the discharge chamber.

Still referring to FIG. 2, a collimating lens 48 is installed adjacent to the discharge chamber 34. Preferably, the collimating lens 48 has a diameter of approximately three to ten millimeters (preferably 5 mm). The collimating lens 48 can be used to collect an emission beam from the discharge gap 40 and focus the beam into an optical fiber 50 having a diameter of approximately two hundred micrometers (200 $\mu$m). It is to be understood that the distance between the front end of the discharge chamber 34 and the collimating lens 48 can be varied from a few mm to 30 mm, and is preferably around fifteen millimeters (15 mm). It is also to be understood that the front end of the discharge chamber can be partly sealed by the collimating lens (as shown in FIG. 2), and also can be fully opened to air with the collimating lens spaced apart from the discharge chamber without any connection between.

FIG. 2 further shows that the housing 12 is formed with a radial bore 52. The device 10 further includes a hollow, generally cylindrical plasma gas tube 54 that defines a proximal end 56 and a distal end 58. The distal end 58 of the plasma gas tube 54 is installed in the radial bore 52 and held firmly in place, e.g., with by a weld, glue, an interference fit, etc. As shown, the plasma gas tube 54 establishes a plasma gas passage 60 having a plasma gas inlet 62 and a plasma gas outlet 64. It is to be understood that the plasma gas tube 54 is in fluid communication with the discharge chamber 34 via the plasma gas passage 60 and provides a plasma gas to the discharge chamber 34. An outlet 66 allows the sample gas and plasma gas to exit discharge chamber 34. Further, the plasma gas tube 54 is in fluid communication with a plasma gas source through a regulator as described below.

Figure 3:
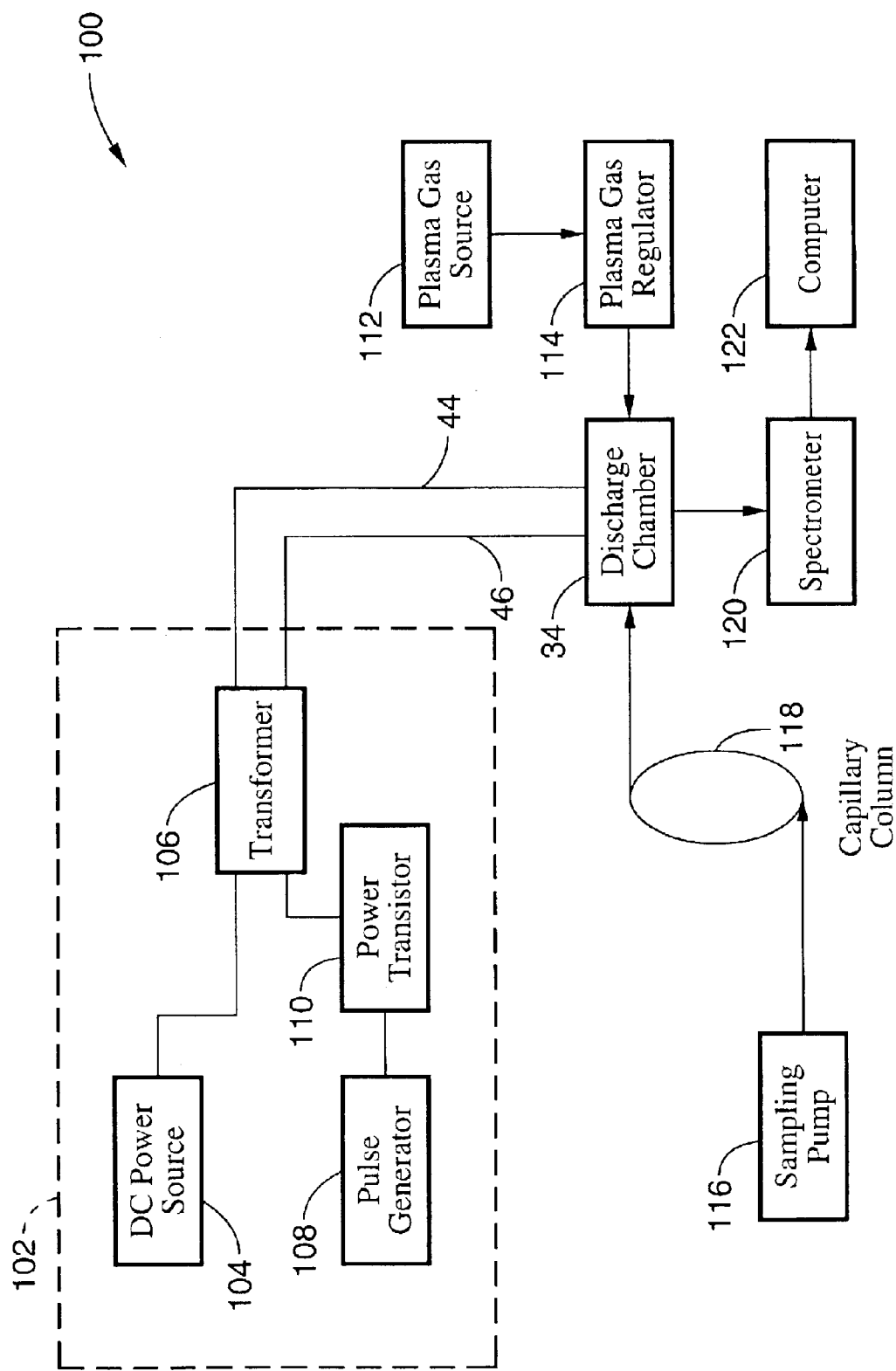
FIG. 3 is a block diagram of a chemical vapor monitoring system according to the present invention with a capillary column for separation.

Referring now to FIG. 3, a chemical vapor monitoring system according to the invention is shown and generally designated 100. FIG. 3 shows that the chemical vapor monitoring system 100 includes a discharge chamber which is preferably the discharge chamber 34 in the handheld/portable detector 10 described above. A power supply 102 is connected to the discharge chamber 34; that is, the power supply 102 is connected to the discharge electrodes 36, 38 (FIG. 2) within the discharge chamber 34 via the conductors 44, 46 (FIG. 2).

As shown in FIG. 3, the power supply 102 includes a direct current (DC) power source 104 that is connected to a transformer 106. The transformer 106, in turn, is connected to the electrodes 36, 38. Preferably, the transformer 106 has a primary voltage, i.e., an output voltage, in the range of approximately 200 V to approximately 1500 V, and a secondary voltage, i.e., an input voltage, of approximately three to approximately 15 V and preferably six and three-tenths volts (6.3 V). It can be appreciated that the DC power source 104 can be one or more alkaline batteries or it can be any other low voltage DC power supply. Moreover, a pulse generator 108 is connected to the transformer 106 via a power transistor 110. Preferably, the pulse generator is an integrated circuit chip that can be used for controlling the time delay or oscillation of the pulses. Further, the power transistor 110 is used to switch the pulse generator 108 on and off.

It is to be understood that with a pulsed power supply to the discharge chamber 34 the power consumption can be decreased substantially. For example, with a duty cycle of ten to one (10:1), the power consumption of a pulsed mode is approximately ten times less than a non-pulsed DC voltage signal. The resulting lower power requirement creates an opportunity to utilize small dry cell batteries to power the microplasma between the electrodes 36, 38. And, a stable pulsed microplasma source can be generated with such a power supply.

FIG. 3 further shows a plasma gas source 112 in fluid communication with the discharge chamber 34 via a plasma gas regulator 114. The plasma gas regulator 114 is in fluid communication with the discharge chamber 34, e.g., by the plasma gas tube 54, described above. It is to be understood that the plasma gas provided by the plasma gas regulator 114 can be used to maintain the microplasma discharge between the electrodes 36, 38. Moreover, the plasma gas can, e.g., be helium, argon, or any other gases such as air. In case of air is used as both plasma gas and measured sample, there is no need of any extra plasma gas source 112 and its regulator 114.

Since the plasma discharge area (e.g., gap 40) is relatively small, e.g., in the micro-liter level, only a small amount of plasma gas is necessary to maintain the microplasma discharge PD. Moreover, since the plasma gases have high excitation potentials and generate highly energized metastable species inside the microplasma, the microplasma discharge PD can provide sufficient energy to excite targeted chemical species through Penning ionization and energy transfer.

Further, it can be appreciated that since the plasma discharge area 40 is very small, the microplasma discharge PD can be sustained with a power as low as tenths milliwatts. This lower power feature allows the discharge chamber 34 (e.g., electrodes 36, 38) and power supply to be powered with a regular dry-cell battery, and thus, makes the detector very portable and flexible for on-site use.

Also, as shown in FIG. 3, a sampling pump 116 is in fluid communication with the discharge chamber 34 via a capillary column 118. The capillary column 118 is in fluid communication with the discharge chamber 34, e.g., by the sample gas tube 20. It can be appreciated that the capillary column 118 can be used to separate the sample gas provided to the discharge chamber 34.

Figure 4:
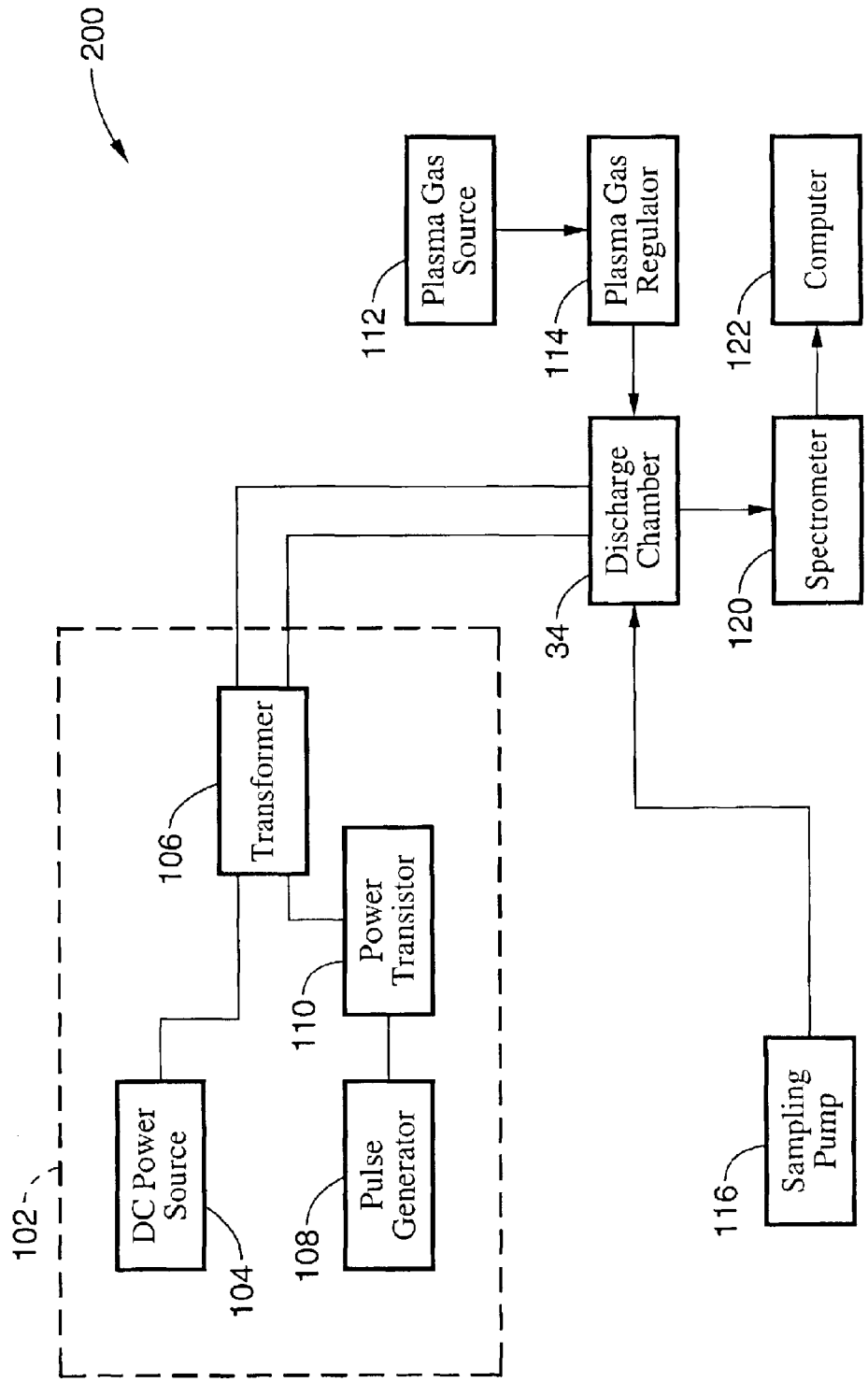
FIG. 4 is a block diagram of a chemical vapor monitoring system according to the present invention with direct sampling through a sampling pump without any primary separation.

Alternatively, as shown in the configuration 200 in FIG. 4, the sampling pump 116 is in fluid communication with the discharge chamber 34 without use of the capillary column 118 shown in FIG. 3. In this embodiment, sampling pump 116 is directly in fluid communication with the discharge chamber 34 (e.g., by the sample gas tube 20). Note that, in this embodiment, there is no sample gas separation before entering to the discharge chamber 34.

FIG. 3 and FIG. 4 further show a spectrometer 120 connected to the discharge chamber 34. It is to be understood that the spectrometer 120 can be connected to the discharge chamber 34 via the optical fiber 50 (FIG. 2) or via direct lens-optical beam focusing (not shown in FIG. 2). In a preferred embodiment, the spectrometer 120 is a palm-sized spectrometer with a ten micrometer (10 $\mu$m) slit. Moreover, a small, linear charge-coupling detector (CCD) is installed in the spectrometer 120 for spectrum measurement. The CCD array sends an analog signal that consists of a stream of voltage levels that are proportional to the light hitting each pixel on the CCD array. Data from the spectrometer 120 can be uploaded to a computer 122, e.g., a laptop, on which the spectrum from the spectrometer 120 can be viewed.

With the configuration of structure described above, the handheld/portable detector for chemical vapor monitoring provides a portable means for sampling chemical vapors. The handheld detector is relatively sensitive, relatively powerful, rugged, and has relatively low power needs. Moreover, the microplasma discharge generated within the discharge chamber 34 has a relatively lower thermal temperature and requires very little power to maintain it, e.g., a small dry cell battery. Also, due to the relatively small volume of the plasma discharge, i.e., in the micro-liter range, a very small amount of plasma gas can be used as a sample carrier and a plasma support gas. Molecular emission spectrum can be collected with a palm-sized spectrometer via a collimating lens and an optical fiber. In turn, this spectrum can be displayed on a notebook computer. With the above-described design and arrangement, the handheld/portable detector 10 and chemical vapor monitoring system 100 of the present invention provides high sensitivity for organic chemical species.

EXAMPLE 1

A detector comprising an air sampling pump for sample introduction, a capillary column for separation, a capillary discharge-based microplasma as energy source for molecular fragmentation and excitation, a small battery powered supply system, and a palm-sized spectrometer for molecular emission detection was constructed as described above. The optical beams were collected from the tiny plasma source through a collimate lens and transferred to the spectrometer with an optical fiber. A Teflon® capillary tube with an inner diameter of approximately 1.5-mm was used as the discharge chamber and two mini-electrodes (Pt) with exposure area of approximately 1-mm$^2$ were placed face to face for generating the plasma. The tiny plasma was formed between the mini-electrodes to provide energy for chemical vapor fragmentation and excitation. The total discharge volume was limited to micro-liter level.

Since the microplasma was sustained in a very small diameter capillary tube, efficiently collecting the optical emission beam was critical to the detector's sensitivity. A small collimating lens with a diameter of approximately 5-mm was used to collect emission beam and focus the beam into an optical fiber with a diameter of 200-$\mu$m. An axial-view mode, head to head, was used in the emission beam collection. The distance between the front end of the discharge chamber and the collimating lens was approximately 15-mm. A palm-sized spectrometer with a 10-$\mu$m slit and 2400-groove grating was used for the detector, making the whole device very compact. A small, linear charge-coupling detector (CCD) array was installed for spectrum measurement. The CCD array was configured to send an analog signal consisting of a stream of voltage levels that are proportional to the light hitting each pixel on the detecting element. Computer software with advanced acquisition and display function was used for data collection and storage and to show the spectrum with a laptop computer.

EXAMPLE 2

Considering a duty cycle of 10:1 in pulse mode, it was assumed that the power consumption in pulse mode was approximately ten times less than that in a DC mode. The lowered power requirement created an opportunity to use small dry-cell batteries to power the plasma. To achieve this goal, a pulsed power supply with small volume and voltage amplification capability was used for the handheld detector. In such a power supply design, a tiny transformer with a primary voltage of 230 V and a secondary voltage of 6.3 V was used to generate high voltage, and a driver circuit was designed for voltage regulation. To achieve a high voltage for the plasma discharge, a low input voltage was applied to the secondary wires of the transformer, allowing to obtain a high output voltage in the primary wires during discharge cycles. Either a low DC power supply or alkaline batteries were sufficient as primary energy source to generate the required pulsed high voltage for the plasma discharge. The duty cycle of the pulse could be modulated with a home-built pulse generator based on a 555 timer, an integrated circuit chip, which is used for controlling time delay or oscillation. A power transistor can be used to switch pulse on and off. A stable pulsed plasma source was be generated with such a power supply. The discharge voltage and current of the plasma could be measured with an oscilloscope if necessary. Both pulsed and DC plasmas were generated and tested with a battery or a low DC power as a primary power source.

EXAMPLE 3

Two sample introduction modes to introduce chemical vapors or air sample into the plasma source for system testing were considered. In the first sampling mode, a carrier/plasma gas was passed through a container in which certain chemical vapor was saturated, and introduced into the plasma. This sampling method can be better served for mono-component chemicals or mixtures with only one significant volatile component. In practical detection or air monitoring processes, such a method can be converted through a small air pump to deliver air samples to mix with plasma gas. The method can be used to answer "yes" or "no" in emergency with a quick response. A small air pump with a volume around one cubic inch and weight of one ounce was installed in the detector. The pumping speed was variable up to approximately 1.5 L/min, and the pump was powered with a regular 12-volt battery. In the second sampling mode, the sample was injected with a syringe and passed through a capillary column (DB-624). In this way, the analyte samples experienced a separation process before reaching the plasma source. With capillary tube sampling as in chromatography, one can identify multiple components based on the retention time of each analyte. However, in such a case, a heating device with temperature control is required for the separation process.

EXAMPLE 4

High purity argon, helium, and nitrogen (99.999%, Trigas Industrial Gases, USA) were used as plasma gases. All chemicals (analytical grade, Aldrich, Milwaukee, USA) for system testing and calibration were used as received without further purification.

EXAMPLE 5

The plasma source was found to be a key feature in handheld/portable detector design. Accordingly, the device was designed with a capillary-discharge based microplasma as an energy source for molecular fragmentation and excitation. Interestingly, the plasma volume was found to be closely related to its characteristics. When the plasma volume is down to micro-liter scale, it possesses some very special features and characteristics, such as low thermal temperature, very low power needs, good plasma density due to the tiny volume, and very low gas flow rate. These features make it possible for the plasma source to be powered with a small dry-cell battery. Such a microscale plasma source could be easily maintained with a small amount of support gas as low as 0.16-ml/s. Since the inert plasma gases have high excitation potentials and generate highly energized metastable species inside the plasma, the plasma source can provide sufficient energy to fragment and excite chemical and biological species through Penning ionization and/or energy transfer. High-energy photons emitted from the plasma source may provide further excitation of the targeted chemical species. With these characteristics, it is ideal to use such a small plasma as an energy source for our handheld detector. It was demonstrated that power consumption in the microplasma was as low as tens of milli-watts when the system is operated in the pulsed mode. This extremely low power can be successfully used to sustain the microplasma source and makes the detector very flexible for on-site use.

EXAMPLE 6

Figure 5:
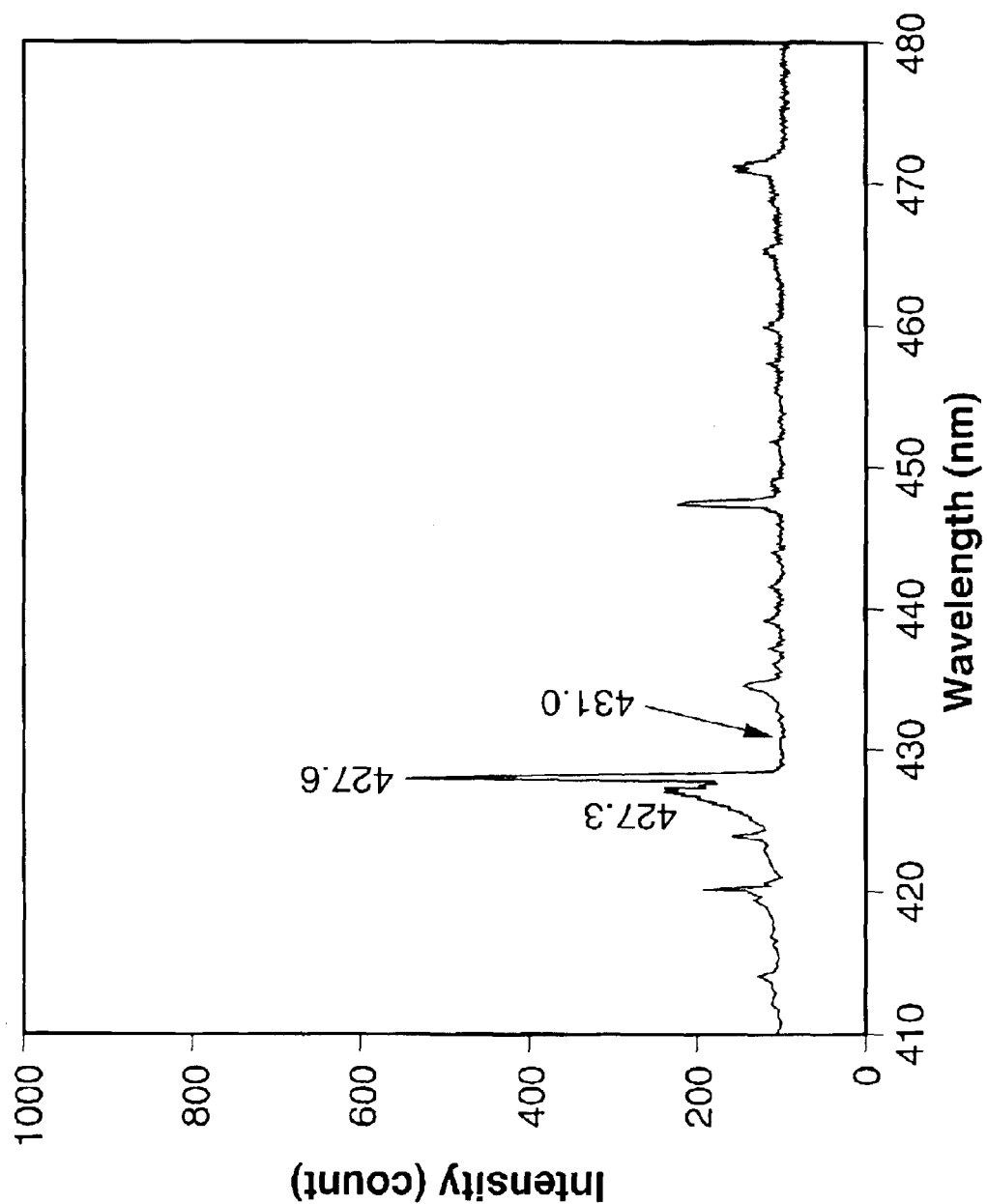
FIG. 5 is a graph showing background emission for a helium plasma source for a discharge voltage of 600V, a helium plasma gas flow rate of 4-ml/s, and a carrier gas flow rate of 0.16-ms/s.
Figure 6:
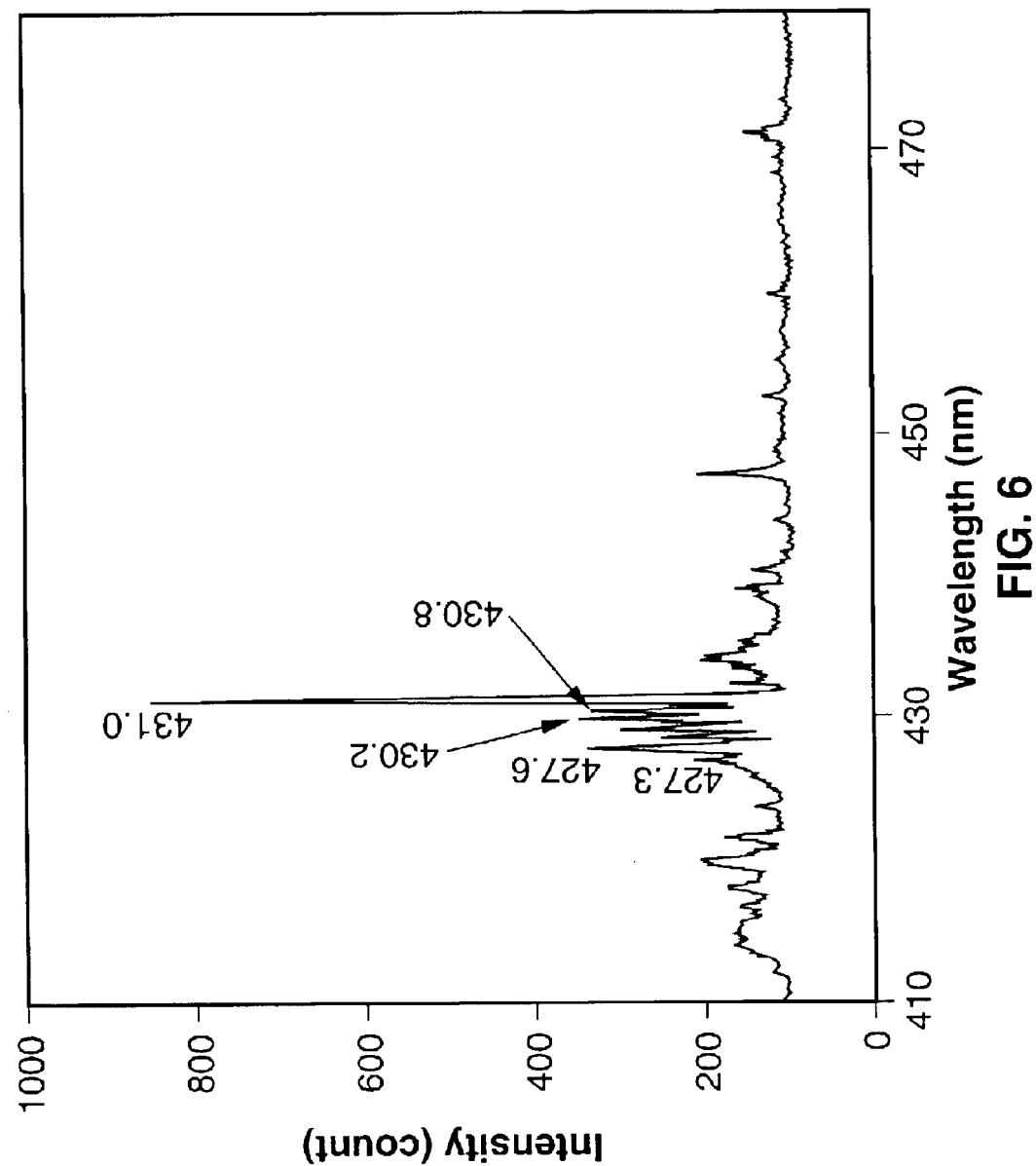
FIG. 6 is a graph showing the dichloromethane spectrum with 2-$\mu l$ vapor sampling for a discharge voltage of 600V, a helium plasma gas flow rate of 4-ml/s, and a carrier gas flow rate of 0.16-ms/s.

Corresponding to each sample introduction method, different spectrum collection approaches were used. With direct pumping of the sample into the plasma without capillary separation (continuous mode), it was possible to collect spectrum in real-time in a wavelength range of interest. FIG. 5 shows the background spectrum obtained with helium plasma gas in a wavelength range from 410-nm to 480-nm, which was found to be of interest. At lower than 410-nm, strong background peaks were found derivated from nitrogen, water vapor, and helium species, like OH, NH, N2, and $N2^+$. A preliminary test showed that organic vapors could give at least several significant peaks in the spectrum range from 350-nm to 500-nm, with most significant peaks at 388-nm and 431-nm. The 431-nm peak, resulting from CH emission, may be the best peak for monitoring as the background influence and contributions at this wavelength are minimal compared with other spectral areas. FIG. 6 shows a typical emission spectrum obtained with saturated methanol vapor using the continuous sampling mode was also observed. Comparing FIG. 5 and FIG. 6, it was found that the distinct 431-nm peak was contributed from methanol's CH emission. The small group peaks from 429.1-nm to 430.8-nm reflected the rotational fine structure of the molecules. Based on these findings, 431-nm was chosen as an analytical wavelength.

EXAMPLE 7

Both pulsed and DC plasmas were tested in a relatively lower power range. At power less than one watt, there was no significant difference between the spectra obtained with each operation mode. However, with the pulsed operation mode, the average power used was significantly lower than that in the DC mode, which created an opportunity to use dry-cell batteries to power the plasma.

EXAMPLE 8

Figure 7:
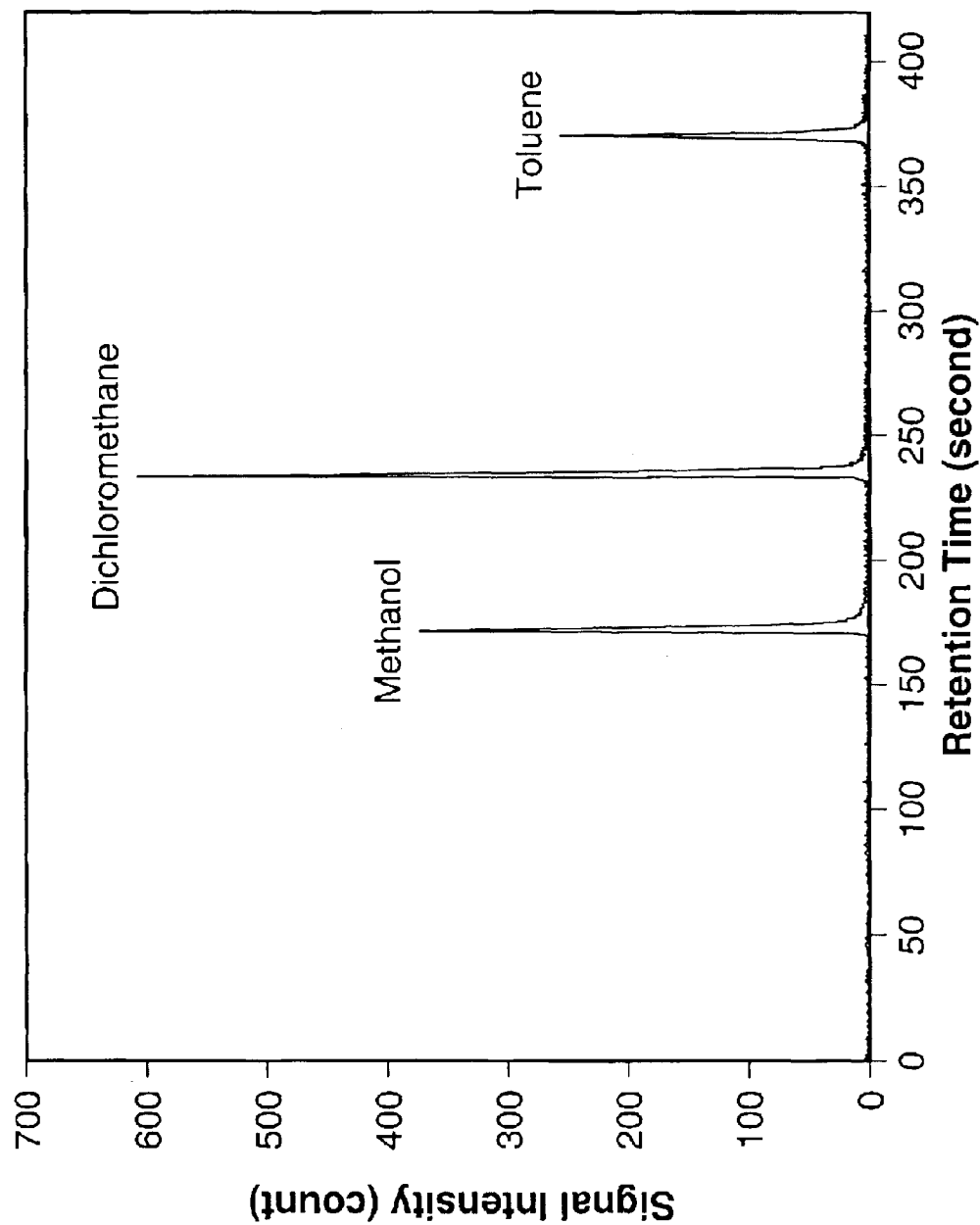
FIG. 7 is a graph illustrating detection of multiple components with capillary column sampling with 2-$\mu l$ vapor sampling for a discharge voltage of 600V, a helium plasma gas flow rate of 4-ml/s, and a carrier gas flow rate of 0.16-ms/s.

With an injection of aliquot vapors into a sampling capillary tube, multiple components were identified through the retention time of each component. By monitoring the peak at 431-nm and using signal intensity vs. retention time, a time-related chromatograph was obtained. A three-component sample of methanol, dichloromethane, and toluene, was prepared by mixing equal liquid volume of each component in a vessel. Assuming equilibrium between the vapors and their bulk liquid after standing for a while, 2-$\mu l$ of saturated vapor was taken with a syringe injector as a sample for capillary sampling. FIG. 7 illustrates a typical example of these three components, obtained with a gradient temperature increase from 40° C. to 120° C. at a temperature increase rate of 10° C. per minute. A commercial capillary column (DB-624) with inner diameter of 0.53-mm was used for sampling and separation in the experiment.

EXAMPLE 9

Figure 8:
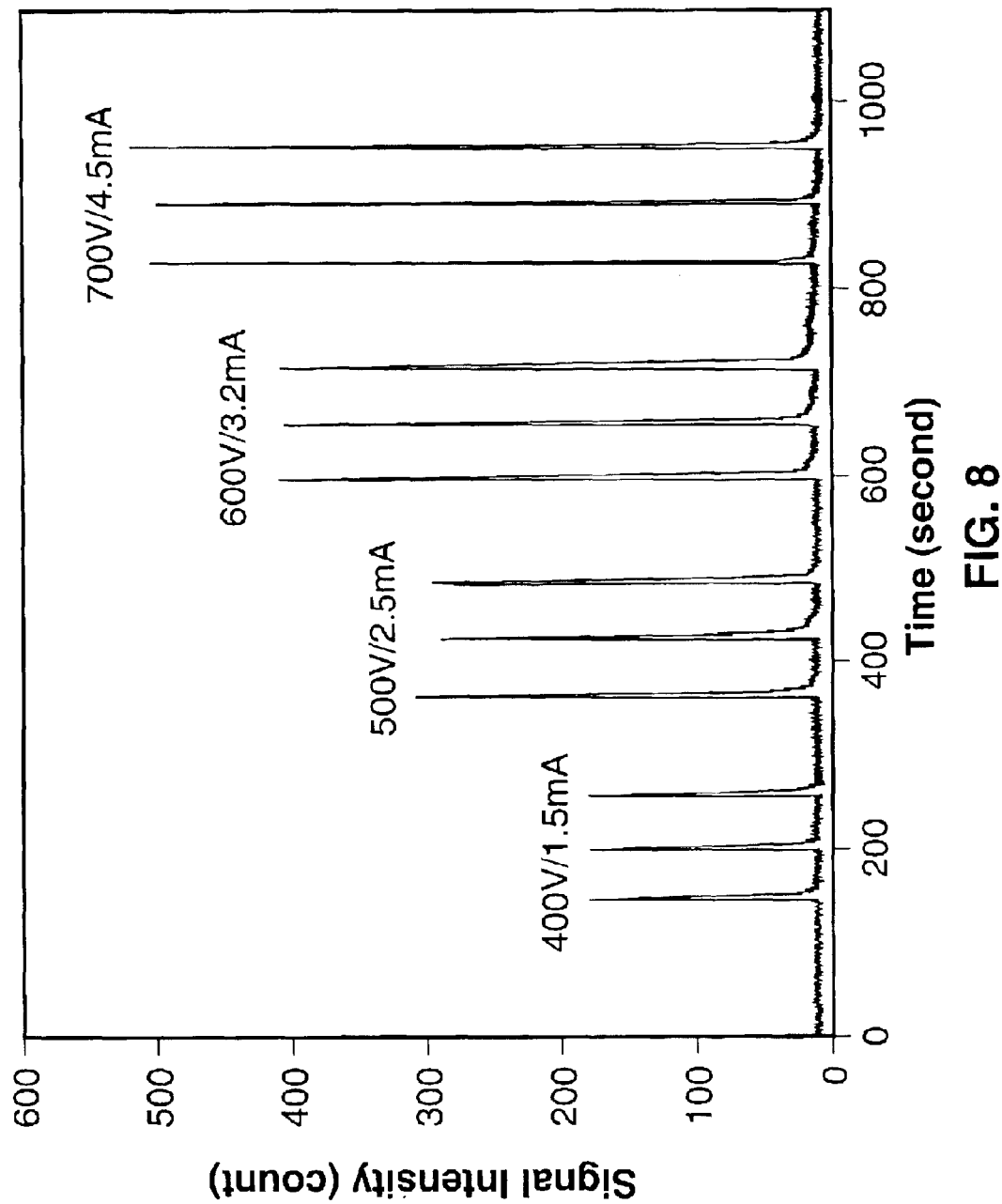
FIG. 8 is a graph showing discharge power influence on methanol signal intensity with the peak monitored at 431-nm with a temperature setting of 75° C., where three replicates were used for each discharge power and where signals were recorded with time change.

Several experimental parameters were tested in this study. An aliquot of 2-$\mu l$ pure methanol vapor (assuming saturated) was used for these examinations. FIG. 8 shows the influence of DC discharge power on signal intensity that was observed. In the relatively low power range tested, increasing discharge power was a benefit for the signal intensity. However, a high power requires a higher energy source and generates extra heat in the discharge chamber, which is considered negative for detector portability. With these concerns in mind, a lower value of the discharge power (less than 1-watt) was determined to be desirable for a field portable detector in cases where battery power is used.

EXAMPLE 10

It was found that the plasma support gas has mixed influence on the system performance. A higher plasma gas flow rate tended to dilute samples from the capillary effluent, but helped to enhance plasma tolerance to air and other foreign materials. In cases where a small sample amount is used, a lower plasma gas flow rate is preferred to enhance signal intensity. However, with large amount of air samples, a certain amount of plasma gas flow rate is required to stabilize the plasma and increase its tolerance. In our work, 4-ml/s plasma gas flow rate is frequently used for detector testing.

EXAMPLE 11

Figure 9:
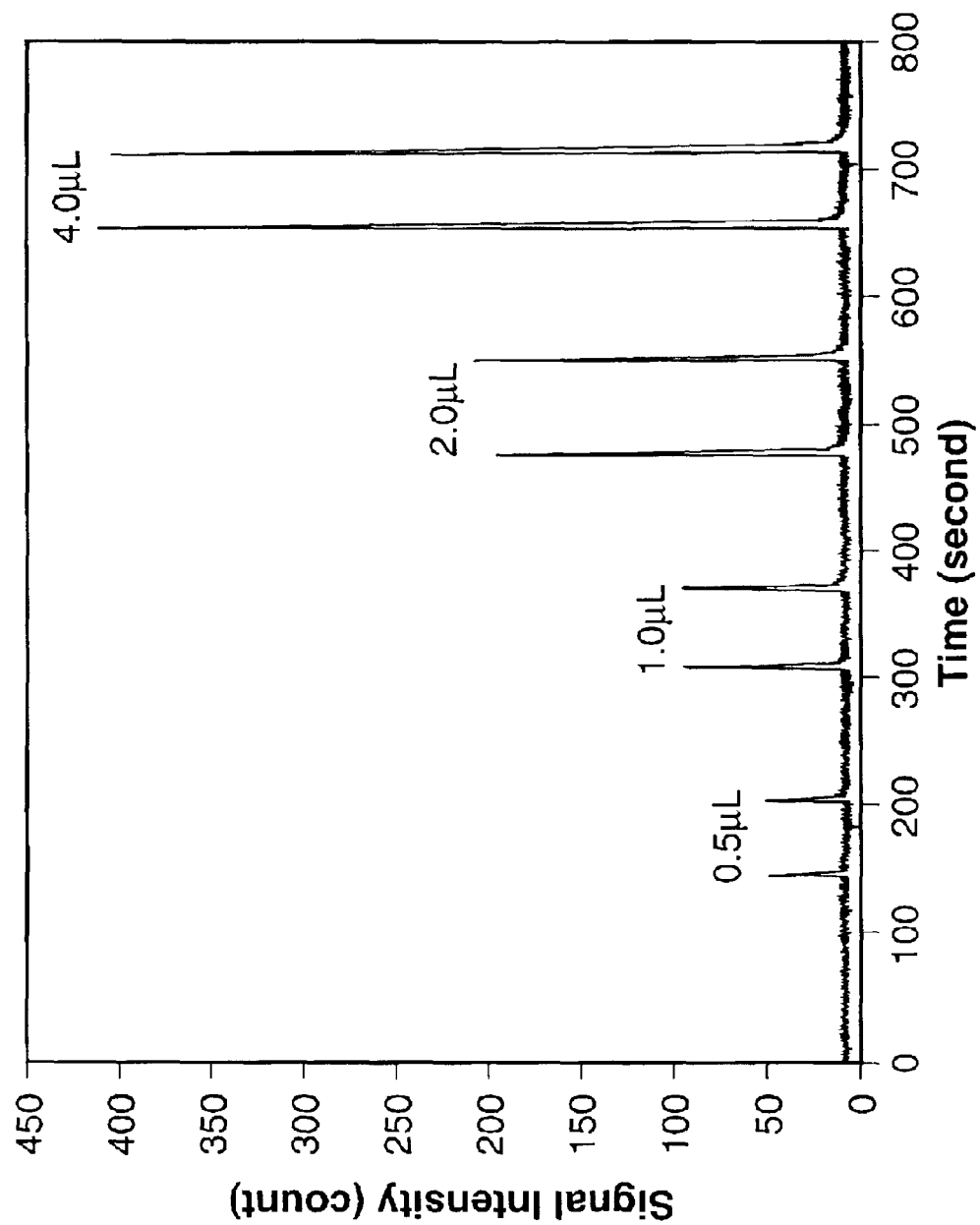
FIG. 9 is a graph showing the relationship between methanol vapor volume and signal intensity with the peak monitored at 431-nm with a temperature setting of 75° C., where three replicates were used for each sample volume and where signals were recorded with time change, for a discharge voltage of 600V, a helium plasma gas flow rate of 4-ml/s, and a carrier gas flow rate of 0.16-ms/s.

Linearity was examined with varied volume of sample vapor. The maximum sample volume tested was 8-$\mu l$. FIG. 9 shows the relationship between vapor volume and signal intensity that was observed. As can be seen, a good linearity was identified with these experimental data.

EXAMPLE 12

Several organic vapors were tested with the detector. A typical vapor sampling volume used was 2-$\mu l$, assuming that the vapor was saturated. The detection limits of these chemical vapors were calculated on the basis of signal intensity and the partial vapor pressure of each component at room temperature. Table 1 gives the results for the three chemicals tested.

TABLE 1

Chemical vapor detection limits with the new detector

| Chemical | Detection limits* | |
|---|---|---|
| | (ng/ml)** | (picogram)*** |
| Methanol | 2.8 | 5.7 |
| Dichrolomethane | 16 | 33 |
| Toluene | 2.6 | 5.3 |

*Calculated based on signal intensity and saturated chemical vapor pressure.
**Detection limits in mass to volume.
***Detection limits in mass.

Table 1 shows the detection limits to be around ppb level in terms of mass to volume, and the absolute mass detection limits are in picogram level. Since an assumption was made in these calculations that the vapor taken from the sample vessel was well saturated, and actually these vapor samples were never saturated when the injector needle was exposed to open air during the injection process, the actual sample injected into the capillary tube is always less than that of the calculated value based on the saturated vapor. Therefore, the detection limits reported here are conservative.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A detector for chemical vapor monitoring, comprising:
   a housing;
   a discharge chamber established within the housing, the discharge chamber having a micro-liter level volume;
   a first electrode disposed within the discharge chamber;
   a second electrode disposed within the discharge chamber, the second electrode being spaced apart from the first electrode;
   a discharge gap established between the first electrode and the second electrode;
   a sample gas tube in fluid communication with the discharge chamber; and
   a plasma gas tube in fluid communication with the discharge chamber;
   wherein the first and second electrodes are configured to generate microplasma to fragment and excite the chemical vapor for detection.

2. A detector as recited in claim 1, wherein the first electrode has a square millimeter ($mm^2$) level exposure area.

3. A detector as recited in claim 1, wherein the second electrode has a square millimeter ($mm^2$) level exposure area.

4. A detector as recited in claim 1, further comprising:
   a collimating lens adjacent to the discharge chamber.

5. A detector as recited in claim 4, further comprising:
   an optical fiber adjacent to the collimating lens, the collimating lens focusing any optical emission beam from the discharge chamber into the optical fiber.

6. A detector as recited in claim 5, further comprising:
   a spectrometer connected to the optical fiber.

7. A detector as recited in claim 6, further comprising:
   a plasma gas source or air providing a plasma gas to the discharge chamber.

8. A detector as recited in claim 7, further comprising:
   a power supply connected to the first electrode and the second electrode, the power supply providing plural voltage pulses to the electrodes, the voltage pulses generating microplasma discharge between the first electrode and the second electrode.

9. A detector as recited in claim 8, wherein the power supply comprises:
   a direct current power source;
   a transformer connected to the direct current power source;
   a power transistor connected to the transformer; and
   a pulse generator connected to the power transistor, the transformer providing plural voltage pulses to the first electrode and the second electrode.

10. A detector for chemical vapor monitoring, comprising:
    a housing; and
    a discharge chamber established within the housing, the discharge chamber having a micro-liter level volume, the discharge chamber generating a microplasma discharge, wherein the discharge chamber receives at least one chemical vapor that is introduced into the microplasma discharge to fragment and excite the chemical vapor for detection.

11. A detector as recited in claim 10, further comprising:
    a first electrode disposed within the discharge chamber; and
    a second electrode disposed within the discharge chamber, the second electrode being slightly spaced from the first electrode.

12. A detector as recited in claim 11, wherein the first electrode has a square millimeter ($mm^2$) level exposure area.

13. A detector as recited in claim 11, wherein the second electrode has a square millimeter ($mm^2$) level exposure area.

14. A detector as recited in claim 11, further comprising:
    a discharge gap established between the first electrode and the second electrode.

15. A detector as recited in claim 11, further comprising:
    a power supply connected to the first electrode and the second electrode, the power supply providing plural voltage pulses to the electrodes, the voltage pulses creating microplasma discharge between the first electrode and the second electrode.

16. A detector as recited in claim 15, wherein the power supply comprises:
    a direct current power source;

a transformer connected to the direct current power source;

a power transistor connected to the transformer; and a pulse generator connected to the power transistor, the transformer providing plural voltage pulses to the first electrode and the second electrode.

17. A detector as recited in claim 10, further comprising:

a sample gas tube in fluid communication with the discharge chamber, the sample gas tube providing the chemical vapor to the discharge chamber.

18. A detector as recited in claim 10, further comprising:

a plasma gas tube in fluid communication with the discharge chamber.

19. A detector as recited in claim 10, further comprising:

a collimating lens adjacent to the discharge chamber.

20. A detector as recited in claim 19, further comprising:

an optical fiber adjacent to the collimating lens, the collimating lens focusing any discharge in the discharge chamber into the optical fiber.

21. A detector as recited in claim 20, further comprising:

a spectrometer connected to the optical fiber.

22. A detector for chemical vapor monitoring, comprising:

a housing;

a discharge chamber established within the housing, the discharge chamber having a micro-liter level volume; and means for generating a microplasma discharge in the discharge chamber to fragment and excite the chemical vapor for detection.

23. A detector as recited in claim 22, further comprising:

means for providing a sample gas to the discharge chamber, the sample gas being introduced into the microplasma discharge to generate optical radiation and/or emission.

24. A detector as recited in claim 23, further comprising:

means for providing a plasma gas to the discharge chamber.

25. A detector as recited in claim 22, further comprising:

means for transmitting the optical emission and/or radiation from the discharge chamber to a spectrometer.

26. A detector as recited in claim 25, further comprising:

means for collimating the optical emission and radiation from the discharge chamber so that it can be transmitted to the spectrometer.

27. A system for monitoring chemical vapor, comprising:

a detector, the detector having a discharge chamber, the plasma discharge chamber having a micro-liter level volume;

a plasma gas source in fluid communication with the discharge chamber;

a sampling pump in fluid communication with the discharge chamber; and a spectrometer optically connected to the discharge chamber;

wherein the plasma chamber is configured to generate microplasma to fragment and excite the chemical vapor for detection.

28. A system as recited in claim 27, further comprising:

a power supply electrically connected to the discharge chamber, the power supply providing plural voltage pulses to the discharge chamber.

29. A system as recited in claim 28, further comprising:

a capillary column in fluid communication with the sampling pump and the discharge chamber.

30. A system as recited in claim 28, wherein the power supply comprises:

a direct current power source;

a transformer connected to the direct current power source;

a power transistor connected to the transformer; and a pulse generator connected to the power transistor, the transformer providing plural voltage pulses to the first electrode and the second electrode.

31. A system as recited in claim 27, wherein the detector comprises:

a housing, the discharge chamber being established within the housing;

a first electrode disposed within the discharge chamber;

a second electrode disposed within the discharge chamber, the second electrode being slightly spaced from the first electrode; and a discharge gap established between the first electrode and the second electrode.

32. A system as recited in claim 31, wherein the first electrode has a square millimeter ($mm^2$) level exposure area.

33. A system as recited in claim 31, wherein the second electrode has a square millimeter ($mm^2$) level exposure area.

34. A system as recited in claim 31, wherein the detector further comprises:

a collimating lens adjacent to the discharge chamber.

35. A system as recited in claim 34, wherein the detector further comprises:

an optical fiber adjacent to the collimating lens, the collimating lens focusing any optical beam from the discharge chamber into the optical fiber.

36. A method for monitoring chemical vapor, comprising:

providing a discharge chamber, the discharge chamber having a micro-liter level volume;

generating microplasma discharge within the discharge chamber;

introducing at least one sample into the microplasma discharge;

fragmenting and exciting the chemical vapor for detection; and measuring the optical radiation emitted by the sample within the microplasma discharge.

37. A method as recited in claim 36, further comprising:

supplying a plasma gas to the discharge chamber.

38. A method as recited in claim 37, further comprising:

establishing a discharge gap between a first electrode and a second electrode within the discharge chamber.

39. A method as recited in claim 38, further comprising:

providing plural voltage pulses to the first electrode and the second electrode to generate the microplasma discharge therebetween.

40. A method as recited in claim 39, wherein the first electrode has a square millimeter ($mm^2$) level exposure area.

41. A method as recited in claim 40, wherein the second electrode has a square millimeter ($mm^2$) level exposure area.

* * * * *